United States Patent [19]

Hoppe

[11] 4,266,935
[45] May 12, 1981

[54] PROTECTIVE SLEEVE FOR THE HANDLE OF A DENTAL INSTRUMENT

[76] Inventor: Gert Hoppe, Hagenstrasse 20 1/2, D-6840 Lampertheim, Fed. Rep. of Germany

[21] Appl. No.: 105,461

[22] Filed: Dec. 26, 1979

Related U.S. Application Data

[63] Continuation-in-part of Ser. No. 62,230, Jul. 30, 1979, abandoned.

[30] Foreign Application Priority Data

Aug. 9, 1978 [DE] Fed. Rep. of Germany ....... 2834797

[51] Int. Cl.³ .............................................. A61C 1/16
[52] U.S. Cl. .................................................. 433/116
[58] Field of Search ........................................ 433/116

[56] References Cited

U.S. PATENT DOCUMENTS

| | | | |
|---|---|---|---|
| 1,682,784 | 9/1928 | Gythfeldt | 433/116 |
| 2,041,077 | 5/1936 | Liningen | 433/116 |
| 2,073,137 | 3/1937 | Bimrose | 433/116 |

*Primary Examiner*—Robert Peshock
*Attorney, Agent, or Firm*—Kurt Kelman

[57] ABSTRACT

A sterilized protective sleeve for the handle of a dental instrument consists of an elastic tubular casing of synthetic resin and adapted to conform to the shank of the instrument. The casing defines a first opening to one end thereof for receiving the shank and enabling the casing to be pulled thereover and a second opening at an opposite end for permitting a tooth treating tool carried on the tip of the shank to project therethrough. A protective member of a shape-retaining resin is mounted on the opposite end and defines the second opening thereon.

3 Claims, 6 Drawing Figures

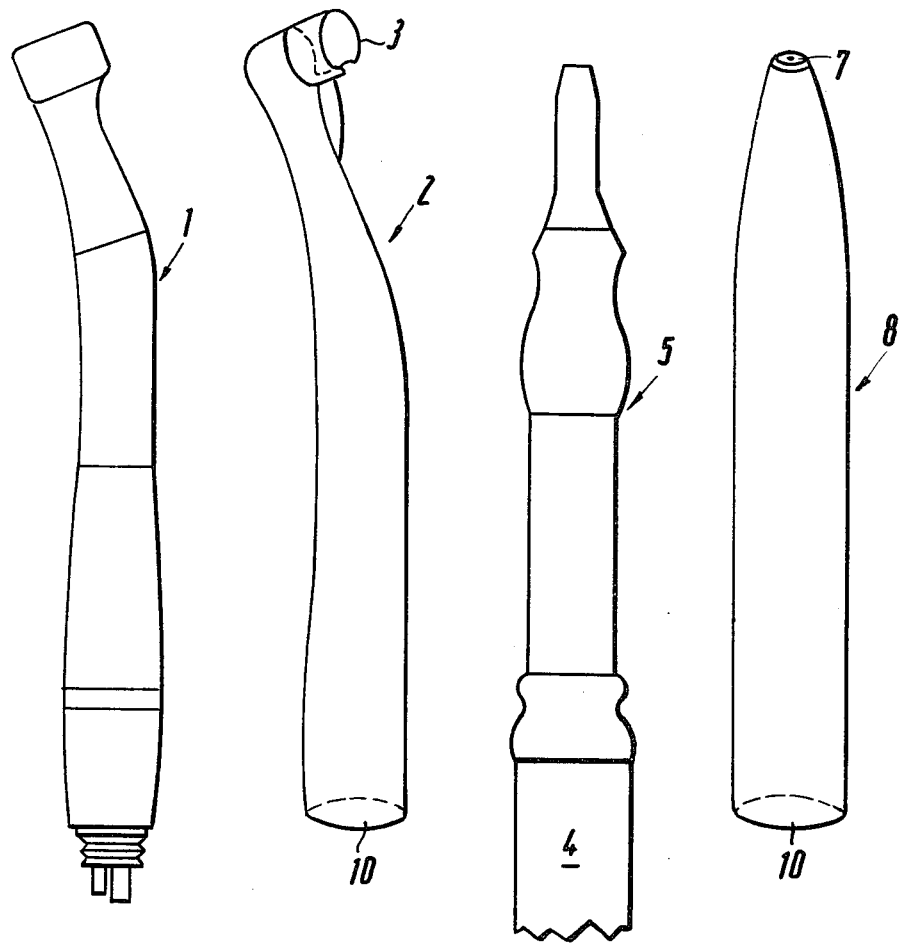
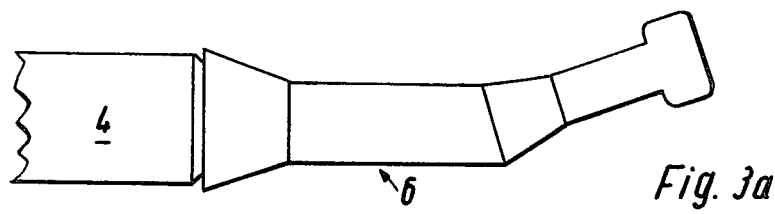
Fig. 3a
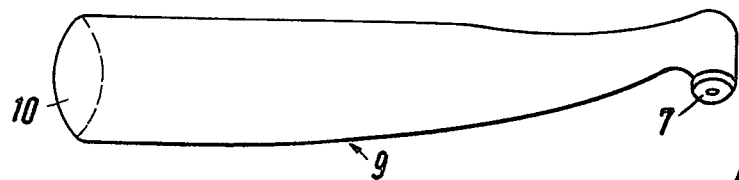
Fig. 3b

PROTECTIVE SLEEVE FOR THE HANDLE OF A DENTAL INSTRUMENT

This is a continuation-in-part of my copending application Ser. No. 62,230, filed July 30, 1979, now abandoned.

The present invention relates to a sterilized protective sleeve for the handle of a dental instrument comprising a shank having a tip for carrying a tooth treating tool, such as a drill, a turbine carrying a drill or the like. The protective sleeve is disposable and may be discarded after each use.

Scrupulous hygiene is of utmost importance in dentistry to avoid infections of the mouth cavity of the patient. Modern dental instruments are very expensive high-precision tools which can be sterilized after the treatment of one patient only with difficulty and with a considerable expenditure of time. If lengthy interruptions are to be avoided, a dentist therefore needs a considerable number of an assortment of such instruments to have at his disposal a required store of sterilized instruments for each patient while the previously used instruments are being sterilized. This may require an available store of about 100 to 150 expensive instruments.

For this reason, the used instrument handles often are not fully sterilized in the dentist's office before being reused but are simply disinfected with a disinfectant spray. Such disinfectants often irritate the skin and, moreover, such a procedure is not comparable in hygienic effectiveness to sterilization which, in case of dental surgery, is absolutely required.

It is the primary object of this invention to protect a previously sterilized handle of a dental instrument against environmental impurities and infectious agents so that the instrument may be used for treating a succession of patients without requiring re-sterilization.

This and other objects and advantages are accomplished according to the invention with a sterilized protective sleeve for the handle of a dental instrument comprising a shank having a tip for carrying a tooth treating tool, the sleeve consisting of an elastic and pliable tubular casing of synthetic resin and adapted to conform to the shank, the tubular casing defining a first opening at one end thereof for receiving the shank and enabling the casing to be pulled thereover and a second opening at an opposite end for permitting the tooth treating tool to project freely therethrough, and a protective member of a shape-retaining synthetic resin mounted on the opposite end of the tubular casing and defining the second opening therein. The opening has a larger radius than the treating tool so that no friction is developed between the rotating treating tool and the protective member.

In use, the handle of the dental instrument is sterilized and, before each patient is treated, the first opening of the tubular casing is placed over the tip of the handle and the casing is pulled over the shank of the handle. Since the casing is adapted to conform to the shank and is pliable and elastic, it will tightly enclose the handle shank, permitting the tooth treating tool, such as a drill or turbine, to project freely through the second opening at the opposite end of the tubular casing. The tubular casing is preferably seamless and, while any suitable elastic synthetic resin may be used, a pliable vinyl polymer, such as polyvinylchloride, has been found very useful.

The above and other objects, advantages and features of the present invention will become more apparent from the following detailed description of certain now preferred embodiments thereof, taken in conjunction with the accompanying schematic drawing wherein FIGS. 1a, 2a and 3a are side views of respective dental instruments and FIGS. 1b, 2b and 3b are side views of respective conforming protective sleeves for these instruments.

As clearly shown in the drawing, each dental instrument comprises a shank having a tip for carrying a tooth treating tool. Dental instrument 1 shown in FIG. 1a is designed to carry a tooth treating turbine 11 carrying drill 12. The conforming protective sleeve 2 illustrated in FIG. 1b consists of an elastic tubular casing of pliable synthetic resin and adapted to conform to the shank. The tubular casing defines first opening 10 at one end thereof and coaxial with the tubular casing. Opening 10 receives the shank of the instrument and enables the casing to be pulled thereover. Protective ring 3 of hard synthetic resin is mounted on the opposite end of the casing and defines a second opening for permitting the tooth treating tool to project therethrough. In this embodiment, wherein the tool is a turbine, protective ring 3 surrounds the turbine head but is radially spaced therefrom so that no heat of friction will develop between the protective ring and the turbine head rotating at high speed. This will prevent melting of the synthetic resin. The protective ring is of a synthetic resin which is shape-retaining but resilient.

The dental instrument 5 of FIG. 2a is designed for carrying a drill 12 on the tip of the instrument shank, the shank being mounted on micromotor 4 driving the drill. Conforming protective sleeve 8 again has a first opening 10 functioning in the above-described manner while plate 7 of hard synthetic resin is mounted on the opposite end of the casing and defines a second opening 7a for permitting the drill 12 to project freely therethrough. The opening in the plate is also coaxial with the tubular casing and the plate protects the bore in the instrument handle which receives the drill.

Dental instrument 6 of FIG. 3a has a shank with a tip extending at substantially right angle from the handle shank for carrying regular or turbine drills driven by micromotor 4. Again, conforming protective sleeve 9 has first opening 10 functioning in the above-described manner, plate 7 also operating as described in connection with FIG. 2b.

The described protective sleeves are sterilized and previously sterilized dental instruments may be readily re-used simply by stripping a used sleeve from the instrument and applying a new one thereover between patients. The disposable tubular casings are inexpensive and no renewed sterilization or disinfection of the instrument is required before the next patient can be treated with the instrument. This enables the dentist to keep a much smaller store of such instruments. Moreover, the protective member will provide the needed protection while being spaced from the rotating treating tool so that the drill may be readily exchanged through the opening in the protective member while the protective sleeve remains on the instrument, and no frictional heat is developed during rotation of the tool, thus preventing the protective member from melting.

What is claimed is:

1. A sterilized protective sleeve for the handle of a dental instrument comprising a shank having a tip for carrying a tooth treating tool which, in turn, has a tool shank comprising:
- a sleeve consisting of an elastic and pliable tubular casing of synthetic resin and adapted to conform to the shank of said instrument, said tubular casing defining a first opening at one end thereof for receiving said instrument shank and enabling the casing to be pulled thereover and a second opening at an opposite end; and
- an annular, disc-shaped protective member integrally attached to said opposite end of said sleeve so that it projects from said second opening, said member being made of a shape-retaining synthetic resin, and having an inner surface defining a through bore configured and dimensioned so as to define a radial clearance sufficient for said tool shank to pass freely and unhindered therethrough.

2. The sterilized protective sleeve of claim 1, wherein the treating tool is a drill and the protective member is a plate having a central opening, the drill projecting freely through the opening in the plate.

3. The sterilized protective sleeve of claim 1, wherein the treating tool is a turbine and the protective member is a ring arranged to surround the turbine.

* * * * *